(12) United States Patent
McGinity et al.

(10) Patent No.: US 9,192,578 B2
(45) Date of Patent: Nov. 24, 2015

(54) HOT-MELT EXTRUSION OF MODIFIED RELEASE MULTI-PARTICULATES

(75) Inventors: James W. McGinity, Austin, TX (US); Sandra U. Schilling, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 423 days.

(21) Appl. No.: 12/544,963

(22) Filed: Aug. 20, 2009

(65) Prior Publication Data
US 2010/0047340 A1 Feb. 25, 2010

Related U.S. Application Data

(60) Provisional application No. 61/090,439, filed on Aug. 20, 2008, provisional application No. 61/107,027, filed on Oct. 21, 2008.

(51) Int. Cl.
| | |
|---|---|
| *A61K 9/16* | (2006.01) |
| *A61K 9/20* | (2006.01) |
| *A61K 31/522* | (2006.01) |
| *B29C 47/00* | (2006.01) |
| *B29K 105/00* | (2006.01) |

(52) U.S. Cl.
CPC ............. *A61K 9/1641* (2013.01); *A61K 9/1694* (2013.01); *A61K 9/2081* (2013.01); *A61K 31/522* (2013.01); *B29C 47/0014* (2013.01); *B29C 47/00* (2013.01); *B29K 2105/0035* (2013.01)

(58) Field of Classification Search
USPC .................................................. 424/457, 473
See application file for complete search history.

(56) References Cited

U.S. PATENT DOCUMENTS

| | | | |
|---|---|---|---|
| 5,552,159 A | 9/1996 | Mueller et al. | |
| 5,958,873 A * | 9/1999 | Sakr et al. ..................... | 514/2.4 |
| 6,335,033 B2 * | 1/2002 | Oshlack et al. ................ | 424/457 |
| 6,488,963 B1 | 12/2002 | McGinity et al. | |
| 6,743,442 B2 | 6/2004 | Oshlack et al. | |
| 7,771,632 B2 | 8/2010 | Ghebre-Sellassie et al. | |
| 2001/0033865 A1 | 10/2001 | Oshlack et al. | |
| 2003/0180362 A1 | 9/2003 | Park et al. | |
| 2003/0219480 A1 | 11/2003 | Fassihi et al. | |
| 2004/0234602 A1 * | 11/2004 | Fischer et al. ................. | 424/473 |
| 2005/0220780 A1 * | 10/2005 | Artamonov et al. ....... | 424/94.63 |
| 2005/0245483 A1 | 11/2005 | Brogmann et al. | |
| 2007/0269484 A1 * | 11/2007 | Hossainy et al. ............. | 424/425 |
| 2007/0298103 A1 | 12/2007 | Hayes | |
| 2008/0026051 A1 * | 1/2008 | Lizio et al. ..................... | 424/452 |

FOREIGN PATENT DOCUMENTS

| | | | |
|---|---|---|---|
| CA | 2229650 | C | 3/1998 |
| CA | 2377301 | A1 | 6/2000 |
| CN | 1795843 | | 7/2006 |
| EP | 0864326 | | 9/1998 |
| EP | 1563897 | A1 | 8/2005 |
| GB | 2196852 | * | 5/1988 |
| RU | 2246293 | | 6/2000 |
| WO | 9818610 | | 5/1998 |
| WO | WO 00/76478 | | 12/2000 |
| WO | 2007001451 | A2 | 1/2007 |
| WO | WO2007001451 | * | 1/2007 |
| WO | 2008101743 | A2 | 8/2008 |
| WO | 2010022193 | A2 | 2/2010 |

OTHER PUBLICATIONS

Chambin et al., Performance of Multilayers ParticlesL Influence of a Thin Cushioning Layer, Drug Development and Industrial Pharmacy, 31: 739-746, 2005.*
Miller at al., Hot-Melt Extrusion for Enhanced Delivery of Drug Particles, Journal of Pharmaceutical Sciences, vol. 96, No. 2, Feb. 2007, p. 361-376.*
Shah et al , Polyox (polyethylene oxide) multifunctional polymer in novel drug delivery system, International Journal of Pharmaceutical Sciences and Drug Research 2014; 6(2): 95-101.*
Janssens et al, Formulation and characterization of ternary solid dispersions made up of Itraconazole and two excipients, TPGS 1000 and PVPVA 64, that were selected based on a supersaturation screening study, European Journal of Pharmaceutics and Biopharmaceutics (2007), doi:10.1016/j.ejpb.2007.11.004.*
Kolter et al, Hot-Melt extrusion with BASF pharma polymers, Extrusion Compendium, 2nd revised and enlarged edition, Oct. 2012, http://www.pharmaingredients.basf.com/Documents/ENP/Brochure/EN/03__120803%20Hot%020Melt%20Extrusion%20with%20BASF%20Pharma%20Polymers.pdf.*
Schmidt et al., A multiparticulate drug-delivery system based on pellets incorporated into congealable polyethylene glycol carrier material, International Journal of Pharmaceutics 216 (2001) 9-16.*
Altaf, S. A., et al., "Bread Compacts. II. Evaluation of Rapidly Disintegrating Nonsegregating Compressed Bread Formulations," Drug Development and Industrial Pharmacy 25:635-642 (1999).

(Continued)

Primary Examiner — Jennifer A Berrios
(74) Attorney, Agent, or Firm — Parker Highlander PLLC (57) ABSTRACT

The present invention includes compositions and methods of making a modified release pharmaceutical formulation and a method of preparation for the embedding of modified release multi-particulates into a polymeric or wax-like matrix. The modified release multi-particulates comprise an effective amount of a therapeutic compound having a known or desired drug-release profile. Modified release multi-particulates may include a polymeric coat or may be incorporated into particle or core material. The polymer matrix comprises a thermoplastic polymer or lipophilic carrier or a mixture thereof that softens or melts at elevated temperature and allows the distribution of the modified release multi-particulates in the polymer matrix during thermal processing. Formulation compounds and processing conditions are selected in a manner to preserve the controlled release characteristics and/or drug-protective properties of the original modified release multi-particulates.

16 Claims, 3 Drawing Sheets

(56) References Cited

OTHER PUBLICATIONS

Beckert, T., E., et al., "Compression of enteric-coated pellets to disintegrating tablets," International Journal of Pharmaceutics 143:13-23 (1996).
Beckert, T. E., et al., "Compression of enteric-coated pellets to disintegrating tablets: uniformity of dosage units," Powder Technology 96:248-254 (1998).
Dashevsky, A., et al., "Compression of pellets coated with various aqueous polymer dispersions," International Journal of Pharmaceutics 279:19-26 (2004).
De Bradbander, C., et al., Development and evaluation of sustained release mini-matrices prepared via hot melt extrusion.
Debunne, A., et al., "Development and in vitro evaluation of an enteric-coated multiparticulate drug delivery system for the administration of piroxicam to dogs," European Journal of Pharmaceutics and Biopharmaceutics 54:343-348 (2002).
Debunne, A., et al., "Compaction of enteric-coated pellets: influence of formulation and process parameters on tablet properties and in vivo evaluation," European Journal of Pharmaceutical Sciences 22:305-314 (2004).
El-Mandi, I. M., Deasy, P. B., "Tableting of coated ketoprofen pellets," J. Microencapsulation 17:133-144 (2000).
Lundqvist, A. E.K., et al., "Compaction of, and drug release from, coated drug pellets mixed with other pellets," European Journal of Pharmaceutics and Biopharmaceutics 46:369-379 (1998).
Schmidt, C., Bodmeier, R., "A multiparticulate drug-delivery system based on pellets incorporated into congealable polyethylene glycol carrier materials," International Journal of Pharmaceutics 216:9-16 (2001).
Tunon, A., Alderborn, G., "Granule deformation and densification during compression of binary mixtures of grandules," International Journal of Pharmaceutics 222:65-76 (2001).
Vergote, G.J., et al., "Wax beads as cushioning agents during the compression of coated diltiazem pellets," European Journal of Pharmaceutical Sciences 17:145-151 (2002).
Wagner, K. G., et al., "Investigation of the pellet-distribution in single tablets via image analysis," European Journal of Pharmaceutics and Biopharmaceutics 47:79-85 (1999).
Yao, T., et al., "Tableting of Coated Particles. II. Influence of Particle Size of Pharmaceutical Additives on Protection of Coating Membrane from Mechanical Damage during Compression Process," Chem. Pharm. Bull. 46:826-830 (1998).
Young, C. R., et al., "Production of spherical pellets by a hot-melt extrusion and spheronization process," International Journal of Pharmaceutics 242:87-92 (2002).
Young, C. R., et al., "Properties of drug-containing spherical pellets produced by a hot-melt extrusion and spheronization process," J. Microencapsulation 20:613-625 (2003).
Young, C. R., et al., "Compression of Controlled-Release Pellets Produced by a Hot-Melt Extrusion and Spheronization Process," Pharmaceutical Development and Technology 1:133-139 (2005).
Young, C. R., et al., "Physicochemical properties of film-coated melt-extruded pellets," Journal of Microencapsulation 24:57-71 (2007).
International Search Report and Written Opinion for PCT/US2009/054374 dated Apr. 2, 2010.
Arzamastsev A.P. "Equivalence of reproductive drugs: pharmaceutical aspects" Vedomosti NC ESMP, 2007, No. 1.
Chueshov et al., "Industrial Technology of Drugs", electronic textbook available from http://www.nuph.edu.ua/ztl/html/medication/, 2010.

* cited by examiner

HOT-MELT EXTRUSION OF MODIFIED RELEASE MULTI-PARTICULATES

CROSS-REFERENCE TO RELATED APPLICATIONS

This application claims benefit of U.S. Provisional applications Ser. Nos. 61/090,439 and 61/107,027 filed on Aug. 20, 2008, and Oct. 21, 2008, respectively which are incorporated herein by reference in their entirety.

TECHNICAL FIELD OF THE INVENTION

The present invention relates in general to the field of controlled release of active agents, and more particularly, to compositions and methods for making hot-melt extrusions including modified release multi-particulates.

STATEMENT OF FEDERALLY FUNDED RESEARCH

None.

BACKGROUND OF THE INVENTION

Without limiting the scope of the invention, its background is described in connection with the controlled release of active agents, e.g., pharmaceutical agents.

One such patent is U.S. Pat. No. 6,335,033, issued to Oshlack, et al. for melt-extrusion of multiparticulates in which a unit dose sustained-release oral dosage form is taught containing a plurality of melt-extruded particles, each consisting essentially of a therapeutically active agent, one or more retardants, and optional water-insoluble binders. The particles have a length of from about 0.1 to about 12 mm and can be of varying diameters and each unit dose provides a release of therapeutically active agents over at least about 8 hours. Methods of preparing the unit doses as well as extrusion processes and methods of treatment are also disclosed. However, the release profile is determined by the type of melt-extrusion. Furthermore, the melt-extrusion process fails to address the need for the release of drugs that are in fragile multiparticulates. The drug release in this patent is governed by the properties of the thermoplastic carrier polymer and not by the particles.

Yet another patent is U.S. Pat. No. 6,743,442, issued to Oshlack, et al. for melt-extruded orally administrable opioid formulations. Briefly, a bioavailable sustained release oral opioid analgesic dosage form is described comprising a plurality of multiparticulates produced via melt extrusion techniques. This patent claims a sustained-release pharmaceutical formulation comprising an extruded blend of a therapeutically active agent, one or more hydrophobic materials selected from the group consisting of alkylcelluloses, acrylic polymers, and mixtures thereof, and one or more hydrophobic fusible carriers having a melting point from about 30° to about 200° C. and selected from the group consisting of natural or synthetic waxes, fatty acids, fatty alcohols, and mixtures thereof, the extruded blend divided into a unit dose containing an effective amount of the therapeutically active agent to render a desired therapeutic effect and providing a sustained-release of the therapeutically active agent for a time period of from about 8 to about 24 hours, the extruded blend being formed by mixing the therapeutically active agent, the one or more hydrophobic materials, and the one or more hydrophobic fusible carriers in an extruder to form the blend and extruding the blend through the extruder. Again, the release profile is determined by the type of melt-extrusion and it fails to address the need for the release of drugs that are in fragile multiparticulates. Again, the drug release in this patent is governed by the properties of the thermoplastic carrier polymer and not by the particles.

One approach as disclosed in patent application WO 2008/101743 (Gryczke 2008) involves the blending of an anionic polymer exhibiting a low glass transition temperature but too high permeability (Eudragit FS) with a water-insoluble polymer (Eudragit RS, RL or NE) to reduce the release in acid.

SUMMARY OF THE INVENTION

This invention provides compositions and methods for their preparation by embedding modified release multi-particulates in a matrix under preservation of the dissolution characteristics of the original modified release multi-particulates. The present invention combines the benefits of a monolithic dosage form that releases multiple unit dosage systems after administration. It has been found that the present invention overcomes some or all of the problems that occur with alternative methods that may be used to formulate modified release multi-particulates into monolithic systems such as compression into tablets or filling into capsules. These shortcomings include one or more of the following: (1) problems of content uniformity of the final product, especially but not only at low loading levels; (2) changes in the drug dissolution profile of the final product compared to the unprocessed multi-particulates due to interference with release controlling principles such as polymeric coating or matrices during the embedment process; (3) limited loading of the monolithic system with multi-particulates due to the requirement of large amounts of excipients to aid the embedment process or to protect the release characteristics of the multi-particulates; (4) sensitivity of the final product to moisture due to the permeability of the matrix-forming principle; and (5) possibility of tampering with the final product.

In one embodiment the present invention describes a controlled release pharmaceutical formulation comprising one or more modified release multi-particulates having an effective amount of one or more therapeutic compounds, wherein the multi-particulates comprise a known drug release profile and are thermally processed into an extrudate in a thermoplastic polymer matrix, a lipid material or both wherein the thermal processing conditions maintain the majority of the known drug release profile of the multi-particulates upon release from the thermoplastic polymer matrix or the lipid material. The extrudate as described in the present invention comprises at least 80% intact multi-particulates, wherein the multi-particulates comprise a polymeric film coat. In one aspect the controlled release pharmaceutical formulation comprising multi-particulates with an inherent drug-release controlling or a drug-protection principle comprises a polymeric matrix or a hydrophobic material. In another aspect the multi-particulates comprise an enteric drug release coating. In yet another aspect the multi-particulates are coated for an extended release and moisture protection of the one or more therapeutic compounds.

In another aspect the modified release multi-particulates are coated with an additional water-soluble or acid-soluble coat and are processed to minimize an incompatibility between the one or more therapeutic compounds and one or more excipients present in the matrix. The water-soluble or acid-soluble coat comprises a polymer selected from the group consisting of polymethacrylates, cellulose derivatives, polysaccharides, proteins, or vinyl polymers. In other aspects the multi-particulates are film-coated drug granules, film-coated drug-loaded pellets or film-coated drug-layered non-pareils. In specific aspects the multi-particulates are in a size range of 50-800 μm, preferably 300-500 μm and the polymeric film coat of the multi-particulates comprises between 10% to 60% polymer(s) (w/w), more preferably 20-50%, based on an uncoated weight of the multi-particulates.

In another aspect the one or more polymers in the polymeric film coat are selected from the group consisting of polymethacrylates, cellulose derivatives, polysaccharides, proteins, or vinyl polymers, and may be plasticized. In yet another aspect the multi-particulates comprise between 5 to 80 weight percent of the one or more therapeutic compounds. In another aspect the thermoplastic polymer matrix comprises one or more components that are at least partially crystalline polymers with a melting point below 80° C. The thermoplastic polymers used in the present invention is selected from the group consisting of poly(ethylene oxide)-poly(propylene oxide) copolymer, poly(ethylene glycol) or poly(ethylene oxide) having a molecular weight less than about 1,000,000. In specific aspects the weight percent of the multi-particulates is 5 to 70 weight percent. The polymer matrix may dissolve, disintegrate or swell in dissolution medium, an aqueous medium to release the modified release multi-particulates or enable drug release from the multi-particulates by diffusion.

The modified release multi-particulates of the present invention are further defined as comprising enteric polymers or water insoluble modified release polymers that control the drug release by diffusion or pH-dependent polymer dissolution. Delayed release articles may be prepared by processing modified release multi-particulates that are enterically coated, with less than 10% drug released in acidic media from the dosage form comprising the enteric coated modified release multi-particulates, and when media is switched to a pH above 6.8, greater than 80% drug is released in 45 minutes in a buffer media outlined in the U.S.P.

In one aspect the modified release multi-particulates further comprise a retardant matrix, wherein the retardant matrix erodes or disintegrates to release the modified release multi-particulates. In another aspect both the matrix and the modified release multi-particulates are film-coated, matrix coated or both.

In another embodiment the present invention is a controlled release pharmaceutical formulation comprising one or more modified release multi-particulates having an effective amount of one or more therapeutic compounds, wherein the multi-particulates comprise a known drug release profile and are thermally processed into an extrudate in a thermoplastic polymer matrix, a lipid material or both, under thermal processing conditions that maintain integrity of the multi-particulates during processing. The extrudate as described by the embodiment of the present invention comprises at least 80% intact multi-particulates.

In another embodiment the present invention discloses a controlled release pharmaceutical formulation comprising one or more modified release pellets with an average particle size of 300-3000 μm, wherein the one or more modified release pellets comprise a pharmaceutically active substance embedded in a matrix of one or more anionic polymers and a processing aid. In one aspect, less than 10% of the pharmaceutically active substance is released after 2 hours in a simulated gastric fluid pH 1.2 and at least 40% after 2 additional hours in a pH 6.8 buffer or a pH 7.4 buffer. In another aspect more than 60% of the pharmaceutically active substance is released after 2 hours in the pH 6.8 buffer or the pH 7.4 buffer.

In a specific aspect the average particle size of the one or more modified release pellets is between 500 and 1000 μm.

The particle size of the one or more modified release pellets as described by the embodiment of the present invention is 200, 300, 400, 500, 600, 750, 800, 1000, 1500, 2000, 2500, 3000 and 5000 μm.

In one aspect a weight percentage of the pharmaceutically active substance is between 0.1-70%. In another aspect the weight percentage of the pharmaceutically active substance is between 5-40%. In yet another aspect the weight percentage of the pharmaceutically active substance is 0.1, 0.5, 1, 2, 3, 4, 5, 10, 20, 30, 40, 50, 60, 70, and 80%. The one or more anionic polymers is a copolymer of methacrylate and methacrylic acid, wherein the one or more anionic polymers are selected from the group consisting of acrylic acid, methyacrylic acid, vinyl acetic acid, crotonic acid, allylacetic acid, 4-methyl-4 pentonic acid, vinyl sulfonate, styrene sulfonate and acrylamido methyl propane sulfonic acid. The copolymer contains at least 20% methacrylic acid.

In one aspect the one or more modified release pellets can withstand a load of at least 10N without undergoing a fracture or a deformation. In another aspect the one or more modified release pellets are transferred to a monolithic system comprising a tablet, a capsule or any combinations thereof.

In one embodiment the present invention describes a method of preparing a controlled release pharmaceutical formulation comprising the step of mixing one or more modified release multi-particulates comprising an effective amount of a therapeutic compound having a known drug release profile with a thermoplastic polymer matrix or hydrophilic wax containing matrix by thermal processing under conditions that preserve a drug-release controlling, a drug-protection characteristic or both of the multi-particulates. In one aspect the thermal processing is performed by a hot-melt extrusion, conducted with a single-screw or a twin screw extruder at temperatures of less than about 100° C.

In another aspect the multi-particulates comprise a film coat that is applied by a dry coating process, an aqueous coating process or by a solvent coating process. In yet another aspect the multi-particulates are coated in a fluidized bed-coater. Sustained release multiparticulates may be obtained by coating with at least one of hydrophobic polymers, hydrophilic polymers, gums, protein derived materials, waxes, shellac, oils and mixtures thereof.

In another embodiment the present invention describes a pharmaceutical solid dosage form providing a controlled release of the therapeutic compound and comprising the pharmaceutical formulation prepared according to the method of the present invention. In one aspect the preferred site of administration of the composition described in the present invention is an oral route. In another aspect the controlled release is further defined as immediate, extended or delayed release.

In yet another embodiment the present invention discloses a method of preparing a controlled release pharmaceutical formulation comprising one or more modified release cylindrical pellets comprising the steps of: (i) mixing a pharmaceutically active substance, one or more anionic polymers, and a processing aid to form a mixture, (ii) processing the mixture with a hot-melt extrusion process to form one or more extruded strands, and (iii) cutting the extruded strand to form the one or more modified release cylindrical pellets. The method as described in the embodiment of the present invention further comprises the steps of applying a polymeric film coat to the one or more modified release cylindrical pellets and spheronizing the one or more modified release cylindrical pellets.

In one aspect the temperature during the hot-melt extrusion process does not exceed 200° C. In another aspect the temperature of at least one of the heating zones during the hot-melt extrusion process exceeds a glass transition temperature of the polymer by at least 10° C.

In one embodiment the present invention is a method for determining one or more extrusion parameters for preparing a controlled release pharmaceutical formulation comprising: selecting one or more modified release multi-particulates with an effective amount of one or more therapeutic compounds having a known drug-release profile, mixing the one or more modified release multi-particulates with a thermoplastic polymer matrix or hydrophilic wax containing matrix, extruding the multi-particulates with the thermoplastic polymer matrix or the hydrophilic wax containing matrix under varying conditions to form an extrudate, determining a drug release profile for the extrudate, and selecting the thermoplastic polymer matrix or the hydrophilic wax containing matrix and the extruding conditions in which at least 80% of the one or more modified release multi-particulates maintain the known drug release profile.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention includes compositions and methods of making a modified release pharmaceutical formulation and a method of preparation for the embedding of modified release multi-particulates into a polymeric or wax-like matrix. The polymer matrix comprises a thermoplastic polymer or lipophilic carrier or a mixture thereof that softens or melts at elevated temperature and allows the distribution of the modified release multi-particulates in the polymer matrix during thermal processing.

The present invention further details a formulation and method of preparation for pellets having a mean particle size of 300-3000 μm, comprising a pharmaceutically active substance in a matrix comprising an anionic polymer and one or more plasticizers. The pellets provide a drug release of less than 10% in simulated gastric fluid over 2 hours, and release at least 40% after another 2 hours in buffer of pH 6.8 and/or pH 7.4.

The preparation of enteric pellets traditionally involves several processing steps including wet-massing and extrusion, spheronization and functional coating. Theses methods require the use of organic or aqueous solvents and time-and cost intensive drying procedures. The pellets manufactured according to these traditional methods usually exhibit low mechanical strength and high friability. The process of hot-melt extrusion of the present invention allows the manufacture of enteric matrix pellets in a single step and continuous manner avoiding subsequent film coating and abstaining from the use of organic solvents. A powder blend comprising the drug, an anionic polymer and optional processing aids is mixed, melted and transported inside a heated barrel by one or two rotating screws before exiting through a product-shaping die. Besides technological advantages, hot-melt extruded pellets allow the incorporation of higher drug loadings under preservation of the controlled release properties which is attributed to the low porosity of melt-extruded matrices when compared to pellets prepared by traditional wet-massing techniques[1]. Melt-extruded pellets further exhibit low friability, high mechanical strength and enhanced robustness of the release properties during downstream processing such as direct compression into single unit tablets[2].

The successful preparation of sustained release pellets by hot-melt extrusion has been reported in several publications[3-5] and patents[6-7]. However, the manufacture of enteric pellets exhibiting a release of less than 10% after 2 hours in simulated gastric fluid remains challenging. Attributed to the larger surface area of small pellets, drug release in acid will be increased when compared to tablets as previously demonstrated for melt extruded Eudragit L100-55 matrices containing 20% drug[8]. Another aggravating circumstance to overcome is the opposing trend between polymer permeability and processability. Anionic polymers with low glass transition temperatures and low melt viscosities produce pellets that are too permeable in acid and release more than 10% of the drug content. On the other hand, polymers exhibiting low permeability and good protection in acid are difficult to process by hot-melt extrusion due to their high glass transition temperature and high melt viscosity.

Dosage forms comprising multi-particulates provide advantages over monolithic dosage forms. These advantages comprise improved distribution along the GI tract and the potential of enhanced bioavailability and more constant blood plasma levels, the avoidance of high local and possible toxic drug concentration, a reduced risk of dose dumping, a decreased susceptibility of the drug absorption to food effects or physiological factors, faster and less variable pharmacological effects due to more reproducible gastric transit times and expanded formulation flexibility by mixing of particles providing different actives or release rates. Post processing of multi-particulates is necessary to provide the patient with a conveniently administrable dosage form. Monolithic systems such as tablets or capsules may be used as the final dosage form and such solid compositions offer advantages over liquid formulations regarding storage stability, safety and patient compliance.

The two most common techniques include the filling of multi-particulates into capsules or the compression into tablets. The applicability of both procedures is compromised due to numerous short-comings. Capsules are more cost-intensive than tablets and may be less secure due to their higher susceptibility to tampering. Capsule shells are hydroscopic and provide little protection to light, oxygen and moisture. They are difficult to open and consequently provide less flexibility in dosing options.

Tabletting involves the exposure of the multi-particulates to high unidirectional compaction forces that may cause coat rupture and/or particle deformation and fracture. It has been reported that a strong particle core is necessary to prevent cracking of Surelease E-7-7050 and Methocel A4C coats applied to Theophylline-comprising pellets[9]. The application of a film coat did not change the strength of the drug pellet, regardless of the coat thickness. The core of the multi-particulates fractured before the coat broke, and was followed by coat rupture when the crushed core was deformed under the compression load. Beckert and coworkers reported an enhanced release of bisacodyl from enteric coated pellets in acidic media when soft pellets with low crushing strength were used as opposed to hard pellets[2].

Sufficient rupture strength of the coat is further necessary to resist film damage at low degrees of particle deformation. Therefore, brittle polymers do not qualify for the application as coating materials unless high coating levels are used. Alternatively, high amounts of plasticizer must be added to increase the film flexibility during compression, but these substances may leach from the product during storage. The flexibility of Eudragit L30D-55 films can further be improved by mixing it with Eudragit NE 30 D, but the drug release during the buffer stage might fail to comply with the USP requirements[10]. Films made with Eudragit L30D-55, only, were too brittle to resist compression induced damage despite plasticization with TEC and relatively high coating level (25%). Pellets coated with Kollicoat 30D MAE 30 DP alone lost their enteric properties after compression because of the brittle character of this polymer, but a mixture of Kollicoat 30D MAE 30 DP and Kollicoat EMM 30D provided sufficient protection in acidic media[11]. Altaf and coworkers reduced the fracture of Aquacoat ECD-30 coats by spray coating the pellet with an additional PEO layer[12]. The swellable polymer hydrated during dissolution and was postulated to act as a sealant for cracks formed in the coat during compression.

The addition of cushioning agents such as wax/starch beads prepared by melt pelletization at a concentration of 50% w/w in the final tablet was demonstrated to reduce damage of diltiazem hydrochloride pellets coated with Eudragit NE 30D[13]. A similar strategy was applied by Debunne and colleagues to retain the dissolution characteristics of coated piroxicam pellets after compression[14]. Enteric pellets coated only with plasticized Eudragit L30D 55 provided sufficient gastric protection over 2 hours, but the amount of waxy pellets was required to exceed the load of functional pellets[15]. Furthermore, the preparation of these cushioning particles is labor and cost intensive and may interfere with the disintegration of the tablet. The utilization of granules with high porosity as tabletting excipient for pellets was also shown to reduce the formation of indentions into the pellet surface, but could not prevent deformation by flattening of surfaces during compression[16]. The efficiency of tabletting additives to act as cushioning agents is further limited by their particle size. A study conducted by Yao et al. with ethylcellulose coated theophylline powder demonstrated that tabletting excipients with smaller particle size were superior to protect the film from damage attributed to their efficient cushioning ability during compression[17].

As detailed above, particle deformation under compression causes rupture of functional films. Film cracking is a function of particle loading in the tablet and limits the applicability of compression methods for high loadings of multi-particulates. It has been reported that up to approximately 30% w/w particle loading-only multi-particulates at the surface are affected by deformation and hence film damage[10]. Higher loading amounts will result in additional particle deformation in the interior of the tablets because the hard particle surfaces are in contact with each other. The disintegration into the individual multi-particulates will further be inhibited by particle fusion during compression. This phenomenon also limits the applicability of high particle loadings.

Tabletting of multi-particulates is further challenging due to differences in particle size, particle shape and true density between the particles and the tabletting additives. The content uniformity of the final dosage form may be compromised by blend segregation and poor powder flow during tabletting. Different strategies have been employed to overcome shortcomings concerning content uniformity such as coating of the tabletting excipients directly onto the coated pellets[18], processing of the tabletting excipients into placebo pellets of the same size[19] or utilizing fillers of small particle size[20]. Most of theses approaches involve further preparation steps resulting in increased operating expenses. Beckert and coworkers investigated the influence of the pellet percentage in the tablet formulation on the content uniformity[21]. The content uniformity was improved by increasing the pellet loading up to 70% and became independent of the filler particle size due to the formation of a percolating cluster of pellets which prevented segregation during compression. At this high loading level, the preparation of tablets became problematic and was only possible when fillers with high binding capacity were utilized. However, tablets containing 10% w/w pellets exhibited high variations in drug content and failed the USP requirements for content uniformity.

Alternatively, enteric pellets may be embedded into tablet-shaped plugs by alternate pouring of a molten carrier and the pellets into molds with cavities[22]. The reported process was manual, discontinuous and needed to be interrupted to allow the carrier to solidify and prevent pellet sedimentation. The study was further limited to polyethylene glycol as the carrier and a pellet load of 8-12% in the matrix.

Thermal processing in general, and hot-melt extrusion in particular, have been adopted from the plastics industry to manufacture matrix systems for pharmaceutical purposes. The therapeutic compound is usually included as a powder or granules into the formulation and dispersed in a molten thermoplastic carrier such as waxes or polymers during processing. The thermal processes involve elevated temperatures and the application of shear forces. Hot-melt extrusion is commonly utilized for the preparation of solid dispersions of poorly soluble compounds. Depending on the solid state of the drug and the number of distinguishable phases in the extrusion product, solid solutions, amorphous mixtures or solid suspensions have been described in the scientific literature. In most cases, the drug particles undergo particle size reduction, melting and/or dissolution in situ, resulting in modified properties of the active compound in the solid dispersion when compared to the bulk material. Amorphization, particle size reduction and hydrophilic coating with the carrier material are the most relevant explanations for the increased dissolution profiles observed for most solid dispersions. A patent filed by Miller, et al., discloses a formulation and preparation method by hot-melt extrusion to disaggregate secondary agglomerates of crystalline or amorphous pre-manufactured drug particles and disperse the individual particles in a carrier under prevention of solid state changes or reaggregation during processing or storage[23]. Upon solidification, the material may be ground into powders for post-processing or cut into tablets, mini-rods or cylinders for post spheronization. Drug release kinetics is controlled mainly by the swelling and erosion kinetics of the carrier material, by the geometry of the dosage form and by the particle size and solid state of the active compound.

As a first step, the modified release multi-particulates comprising the therapeutic compound are prepared. Next, these modified release multi-particulates are blended with one or more extrudable agents and are extruded, e.g., hot-melt extruded, into a final formulation in which at least 50, 60, 70, 80, 90 or a higher percentage of the modified release multi-particulates release their active or therapeutic agent with the same or equivalent release profile as before the extrusion upon release from the extrusion matrix. Alternatively, the drug release may additionally be controlled by the nature of the extruded matrix. For example, if the final formulation includes an extrudable matrix that releases the modified release multi-particulates after, e.g., traversing the stomach, the release of the active ingredient will be controlled by the matrix and by the properties of the modified release multi-particulates.

As used herein, the term "multi-particulates" refers to one or more unit dosage systems such as, but not limited to, pellets, beads, spheres, mini-tablets, seeds, spheroids or granules with modified drug release profile. The multi-particulates comprise a drug-release controlling and/or drug-protecting film or matrix, such as a polymeric film or matrix, whose intactness or efficiency is susceptible to certain conditions such as heat or mechanical forces that may occur during post-processing. The expression "core material" describes the nature of the interior part of multi-particulates that may also comprise a functional coat. Exemplary "core-materials" may be pellets (spherical matrix systems that contain a drug and further excipients), granules (less spherical particles that are almost entirely composed of drug) or nonpareils (spherical particles without drug).

The terms "therapeutic compound", "drug" and "active pharmaceutical ingredient" are used interchangeably to refer to chemical entities that display certain pharmacological effects in a body and are administered for such purpose.

Non-limiting examples of therapeutic compounds include, but are not limited to, antibiotics, analgesics, vaccines, anti-convulsants; anti-diabetic agents, antifungal agents, antineoplastic agents, anti-parkinsonian agents, anti-rheumatic agents, appetite suppressants, biological response modifiers, cardiovascular agents, central nervous system stimulants, contraceptive agents, dietary supplements, vitamins, minerals, lipids, saccharides, metals, amino acids (and precursors), nucleic acids and precursors, contrast agents, diagnostic agents, dopamine receptor agonists, erectile dysfunction agents, fertility agents, gastrointestinal agents, hormones, immunomodulators, antihypercalcemia agents, mast cell stabilizers, muscle relaxants, nutritional agents, ophthalmic agents, osteoporosis agents, psychotherapeutic agents, parasympathomimetic agents, parasympatholytic agents, respiratory agents, sedative hypnotic agents, skin and mucous membrane agents, smoking cessation agents, steroids, sympatholytic agents, urinary tract agents, uterine relaxants, vaginal agents, vasodilator, anti-hypertensive, hyperthyroids, anti-hyperthyroids, anti-asthmatics and vertigo agents. In certain embodiments, the one or more therapeutic compounds are water-soluble, poorly water-soluble drug or a drug with a low, medium or high melting point. The therapeutic compounds may be provided with or without a stabilizing salt or salts.

As used herein, the term "friability" refers to the tendency for the multi-particulates or particles of the present invention to disintegrate, break, rupture or for coatings to rub-off or break-off from attrition during processing or handling. In the present invention, if such friability of the multi-particulates occurs, such particles will fail to provide the required therapeutic compound (or drug) release and the dosage form will be unusable. The present invention provides a significant advantage over the prior art because the thermal conditions selected for the co-extrusion of the thermal matrix and the multi-particulates reduce or mostly eliminate the friability of the multi-particulates extruded into the extrusion matrix, thereby having the advantage of combining the release profiles of both the extruded matrix and the multi-particulate. In certain cases, the friability of the multi-particulate will be determined by the manner in which the multi-particulate was processed or formed, the manner in which the multi-particulates were coated or composition of the coating (if any). Accordingly, the composition of the coating (or shell), e.g., the powder(s), shell(s), coating(s), binder(s), polymer(s) and or excipient(s) are selected so that the finished product has at least a moderate amount of resistance to chipping, breakage, attrition, friction, and the like. Material selections for achieving this are known in the art and are further described in the Examples.

Various methods of preparation may be used to manufacture the drug containing particles and high mechanical strengths are not necessary. Exemplary methods of preparation comprise wet-mass extrusion and spheronization, wet granulation and spray layering. Other methods including hot melt extrusion, compression molding or similar thermal processes can be used.

A polymeric coat may be applied to the core material to modify the drug release and/or to separate the drug from its environment for protection. The coating level should be greater than 10% and, more preferably, greater than 20% w/w polymer weight gain, to ensure its stability during thermal processing. The application of polymers with glass transition temperatures that are higher than the thermal processing temperature may be necessary to prevent in-situ softening of the coat. However, optimization of the formulation will minimize the period of exposure of the multi-particulates to elevated temperature and render this requirement redundant. Optionally, an additional water-soluble or acid soluble coat may be applied on top of the release-modifying coat to act as a barrier between the release-modifying coat and the carrier matrix. Non-limiting examples of polymers that may be included in the top coat are hydroxypropyl cellulose, hypromellose, hydroxyethyl cellulose, methylcellulose, carboxymethylcellulose sodium, dimethylaminoethyl methacrylate methylmethacrylate copolymer, chitosan, polyvinyl alcohol or polyvinylpyrrolidone.

All excipients and therapeutic compounds present in the multi-particulates should further exhibit sufficient thermal stability under the applied temperatures.

Particle size requirements for the multi-particulates depend strongly on the selected method and processing conditions and, in the case of hot-melt extrusion, on the configuration of the extrusion equipment. Particles not exceeding about 800 µm with a preferred size range of about 300-500 µm are most suitable for processing by hot-melt extrusion. Single screw extruders may have certain advantages over twin-screw extruders, however, the goal is to preserve the original particle characteristics during thermal processing.

The carrier matrix comprises at least one thermoplastic polymer or meltable lipid, and may also contain further functional excipients such as disintegrants, glidants, plasticizers, antioxidants, retardants or other release-modifying agents, surfactants, stabilizing agents or processing aids. The term "matrix" relates to the material surrounding the multi-particulates to provide a multi-particulate dosage form.

The term, "thermoplastic" when describing a polymer refers to one or more polymers that melt and/or soften when heat is applied to allow molding while maintaining good chemical stability. Exemplary thermoplastic polymers that may be used as matrix material include, but are not limited to, poly(ethylene oxide)-poly(propylene oxide) copolymer, poly(ethylene glycol), poly(ethylene oxide), poly(vinyl alcohol), carbomer, polycarbophil, cellulosic derivatives, natural gums, povidone, poly(vinyl acetate), alginates, acrylic and methacrylic polymers. Lipids include waxes such as beeswax, carnauba wax, glycerides (mono, di- and tri-), GMS, GMO, sucrose stearate. It is contemplated and within the scope of the invention that a combination of appropriate polymers and/or lipids may be used as matrix material in form of copolymers or physical blends.

The multi-particulates may be blended with the carrier polymer prior to extrusion, or be dosed to the carrier during the extrusion process using a separate port along the barrel. Feeding the multi-particulates over a port that is located in the vicinity of the die zone may reduce the exposure of the particles to thermal stress and shear forces and may promote the physical and functional intactness of the multi-particulates.

Under the conditions of thermal processing, the multi-particulates must remain generally physically intact so that the drug release characteristics of the original particles are preserved in the matrix product. This is achieved by utilizing a carrier polymer that meets one or more of the following requirements: Melting or softening at relatively low temperatures so that the integrity of the multi-particulates is not compromised by thermally induced processes such as softening, deformation, dissolution in the carrier polymer or chemical degradation whose likelihood increases as a function of temperature. Low melt-viscosity to provide low resistance against the rotation of the screw during hot-melt extrusion and to minimize the shear forces exerted on the multi-particulates. Good flowability in the solid state and low melt-viscosity to facilitate rapid transit through the extruder barrel and reduce the residence time of the composition inside the extruder barrel and hence the time of material exposure to elevated temperatures. Especially prill grades yield excellent flowability. Similarity with the multi-particulates regarding particle size, spherical shape and true density to avoid blend segregation and ensure content uniformity of the final product. A low degree of intermolecular interaction with the excipients in the multi-particulates that get in direct contact with the thermoplastic carrier during extrusion.

The resulting matrix system can be produced in strands, cylinders, tablets, hollow tubes or films. Post-processing may include various product-shaping technologies such as pelletization or other cutting techniques, calendering, molding or spheronization to produce a dosage form of the desired geometry.

The final dosage form will exhibit properties that are comparable to the unprocessed multi-particulates in terms of controlled release of the drug and/or its protection from environmental influences. As used herein, the terms "modified release" and "controlled release" are interchangeable and intended to describe immediate, extended or delayed drug release profiles as used in the USP 31 [24] and necessitates the presence of a release controlling element. The release controlling element may be a functional coat and/or may be provided by the matrix material.

The present invention further discloses a formulation and a method of preparation for the hot-melt extrusion of enteric matrix pellets. The pellets as described in the present invention have an average particle size between 500 and 3000 µm, preferably between 500 and 1000 µm and comprise a pharmaceutically active substance (drug) in a plasticized, anionic polymer matrix. The herein disclosed pellets release less than 10% of the drug after 2 hours in simulated gastric fluid pH 1.2, and more than 40% after an additional 2 hours in buffer pH 6.8 or 7.4, respectively. The herein disclosed pellets further exhibit high mechanical strength and low friability that makes them more suitable for post-processing than pellets prepared by traditional methods. Examples for post-processing comprise functional film coating, direct compression, filling into capsules and melt extrusion into monolithic systems.

Anionic polymers contain anionic groups that are protonated during the acidic stage, but ionize after pH increase. The anionic polymer that is used as the release controlling matrix is insoluble at low pH and exhibits a low permeability for the drug in the acidic stage of dissolution testing. During the buffer stage, ionization of the acidic groups of the polymer will increase the drug release by matrix swelling and/or erosion. Especially suitable are copolymers of methacrylate and methacrylic acid of varying ratios (Eudragit S and Eudragit L) or mixtures thereof.

Pharmaceutically acceptable anionic polymers used for the melt extrusion process possess high glass transition temperatures and high melt viscosities at processing conditions. According to the invention, acceptable plasticizers or plasticizer mixtures are added to the formulation in sufficient amount to decrease the glass transition temperature and the melt viscosity of the polymer to avoid thermal degradation as occurring at elevated processing temperatures. Acceptable plasticizers are non-toxic and regarded as safe, exhibit high plasticization efficiency for the anionic polymer and do not increase the drug release above 10% during the acidic stage.

The pellets may comprise one or several pharmaceutically active substances at a combined level of about 0.1 to 70%, preferably 5 to 40% drug. The pellet formulation may further comprise additional excipients and/or processing aids improving the chemical stability, processability or release properties of the pellets such as thermal lubricants, glidants and/or antioxidants.

The process of hot-melt extrusion of the present invention is advantageous over traditional pellet preparation methods since it is a one-step, continuous process avoiding the use of solvents or labor-intensive drying procedures. The components of the disclosed composition may be reduced in particle size and/or blended prior to extrusion utilizing commonly available milling and mixing equipment. Commonly used single or twin screw extruders of varying sizes and with one or several temperature zones may be used according to the invention. The temperature of at least one of the heating zones must be selected to be at least 10, preferably at least 30° C. above the glass transition temperature of the plasticized polymer to produce a polymer melt of sufficiently low melt viscosity. The extrusion temperature must further be below the thermal degradation temperature of the polymer or of the other formulation components. The diameter and shape of the extruded strand is primarily governed by the diameter and geometry of the die orifice, but may also be influenced by the viscoelastic properties of the polymeric melt. Circular dies with diameters between 500 and 1000 μm are preferred according to the present invention. The extruded strands may be cut into cylindrical pellets in the hot state or after cooling to room temperature and may further be spheronized. Several technologies have been developed for the subsequent pelletization and spheronization in a continuous or semi-continuous manner[25-27].

The terms "enteric dissolution testing" and "enteric drug release" are interpreted as described in USP 31 chapter <711> for delayed-release dosage forms[24].

The term "extended drug release" is used as described in USP chapter <711> for extended-release dosage forms[24].

EXAMPLE 1

Core Materials

TABLE 1

Examples for core materials that may be used for the preparation of modified release multi-particulates. (Moisture content determined as loss on drying of coated, cured particles after equilibration at 22 ± 1° C. and 50 ± 5% RH (n = 3).)

| Core Material | Supplier | Theophylline Content [%] | Moisture Content [%] |
|---|---|---|---|
| Drug Granules | BASF | 99.5 | 2.15 ± 0.13 |
| Pellets | Self-made according to example 2 | 30.0 | 3.52 ± 0.08 |
| MCC Spheres | Asahi Kasei (Celphere ® CP-305) | 10.8 | 3.50 ± 0.25 |

EXAMPLE 2

Preparation of Pellets

The following procedure may be used to prepare pellets of the desired particle size. The drug and microcrystalline cellulose were placed in a bowl and thoroughly premixed for 10 minutes. The PVP K25 was dissolved in the water, and this binder solution is added dropwise to the powder under stirring. The wet-massed material was then transferred into a LCI Benchtop granulator and extruded through a 0.6 mm screen at a rotation blade speed of 50 rpm. The extruded strands were placed in a Caleva Model 120 Spheronizer and rotated at 700 rpm for 3 minutes. The obtained pellets were dried in a 40° oven for 24 hours and sieved. The fraction between 300 and 500 μm was used for subsequent enteric coating.

TABLE 2

Formulation for the preparation of pellets.

| Component | Quantity [g] | Percentage |
|---|---|---|
| Anhydrous theophylline | 90.0 | 30.0% |
| Microcrystalline cellulose (PH101) | 187.5 | 62.5% |
| PVP K25 | 22.5 | 7.5% |
| Water dest. | 180.0 | |

EXAMPLE 3

Drug Layering of Nonpareils

Active layered nonpareils of the desired particle size range were prepared utilizing the following procedure.

TABLE 3

Coating dispersion for 30% drug weight gain of a 250 g batch.

| Component | Quantity [g] |
|---|---|
| Anhydrous theophylline | 75.0 |
| HPMC E3 (Pharmacoat 603) | 8.0 |
| Talc | 20.0 |
| Water dest. | 425.3 |

A 250 g batch of nonpareils made of 100% microcrystalline cellulose NF and having a particle size of 300-500 μm (Celphere® CP 305, Asahi Kasei America, Inc.) were introduced in a Strea-1 fluidized bed coater (Aeromatic-Fielder) and layered with an aqueous dispersion of Theophylline and HPMC E3 applying the following conditions:

TABLE 4

Process parameters for Strea-1 fluidized bed coater (Aeromatic-Fielder).

| Batch size | 250 g |
| Theoretical drug weight gain | 30% |
| Atomizing air pressure | 1.5-1.8 bar |
| Fan capacity | 3-6 |
| Nozzle diameter | 1.0 mm |
| Inlet temperature | 75-80° C. |
| Outlet temperature | 45-50° C. |
| Spray rate | 2.0 g/min or 8.0 g/min * kg |
| Spray mode | bottom, Wurster column |

The obtained layered particles were dried (24 hours in 40° C. oven) and sieved prior to enteric coating.

EXAMPLE 4

Enteric Coating of Core Material

The following formulation and processing method may be employed to provide the core material (pellets, granules, nonpareils) with an enteric coat. Alternative functional polymers, plasticizers or anti-tacking agents may be used. The film coated particles may be dried overnight in a 40° C. oven or inside the coater, sieved and the 300-500 μm particle size fraction may be used for subsequent hot-melt extrusion.

TABLE 5

Coating dispersion for 200 g batch.

| Formulation | Percentage | Amount [g] |
|---|---|---|
| Eudragit ® L30D-55 | 12% polymer in dispersion | 400 (120 g polymer) |
| TEC | 10% based on polymer content | 12 |
| GMS | 7.5% based on polymer content | 9 |
| Tween 80 | 40% based on GMS | 3.6 |
| Water | | 575.4 |
| Solid content | 14.46% | |

TABLE 6

Process parameters for functional coating in a Strea-1 fluidized bed coater (Aeromatic-Fielder).

| | |
|---|---|
| Weight gain | 20-50% |
| Inlet temperature | 36-38° C. |
| Exhaust temperature | 32-33° C. |
| Nozzle diameter | 1.0 mm |
| Spray rate | 10 g/(min * kg) |
| Set-up | Wurster, bottom spray |

Additional polymeric top coats may be applied to the enteric coated multi-particulates to improve their resistance to high temperatures and/or shear forces during the subsequent hot-melt extrusion process.

EXAMPLE 5

Hot-melt Extrusion of Enteric Matrix Pellets

The following formulations and procedure may be used to prepare enteric matrix pellets of the desired particle size. Powder blends for extrusion were prepared by pre-mixing the polymer with the plasticizer and subsequent blending with the drug using appropriate mixing equipment. A mini extruder equipped with two co-rotating screws and a circular 500 μm die (Haake Minilab, Rheomax CTW5, Thermo Electron, Germany) may be used for the preparation of the drug loaded, polymeric strands, which were then cut to obtain cylindrical pellets. The pellets may be spheronized in a subsequent step employing appropriate spheronization equipment.

TABLE 7

Examples for the formulation of enteric matrix pellets.

| Plasticizer | Plasticizer Amount [%] | Eudragit ® S 100 [%] | Theophylline [%] | Extrusion Temperature [° C.] |
|---|---|---|---|---|
| none | 0 | 70 | 30 | 220 |
| TEC | 10 | 60 | 30 | 180 |
| TEC | 20 | 50 | 30 | 140 |
| PEG 8000 | 10 | 60 | 30 | 180 |
| PEG 8000 | 20 | 50 | 30 | 140 |
| Methylparaben | 10 | 60 | 30 | 180 |
| Methylparaben | 20 | 50 | 30 | 140 |

EXAMPLE 6

In vitro Method Drug Release Testing of Enteric Matrix Pellets

The drug release properties from the pellets may be determined as described in USP 31, method <711> for delayed-release dosage forms method A. A paddle set-up (apparatus 2) was employed with a water bath to maintain the media temperature at 37±0.5° C. and the paddle speed set to 50 rpm. The formulations were placed in 750 ml simulated gastric fluid pH 1.2 (without pepsin, referred to as acid stage) for 2 hours and an aliquot of the fluid was withdrawn at the end of this period. A volume of 250 ml 0.20 M tribasic sodium phosphate that had been equilibrated to 37±0.5° C. was added after 2 hours to raise the pH of the media to 6.8 or 7.4, respectively (buffer stage). After expiration of the testing period, the remaining particles were completely destroyed by mixing with a high shear homogenizer to completely release residual drug, an aliquot of the fluid was filtered and analyzed to determine the total amount released using a validated HPLC method. All average values were obtained from at least n=3 and were reported as % released from the total amount released.

TABLE 8

Drug release of melt extruded pellets (formulations according to invention are in bold type).

| Formulation | SGF 2 hrs | Buffer 45 min | Buffer 2 hrs | Buffer 4 hrs | Buffer 6 hrs | Buffer 8 hrs | Buffer 10 hrs |
|---|---|---|---|---|---|---|---|
| 10% Theophylline 75% HPMC AS LF 15% TEC | 27.2 | 81.3 | 98.8 | | | | |
| 10% Theophylline 78.2% HPMC AS LF 11.8% PEO 200K | 28.3 | 77.5 | 92.8 | | | | |
| 10% Theophylline 60% HPMC AS LF 15% Ethylcellulose 15% ATBC | 13.9 | 90.2 | 97.7 | | | | |
| 10% Theophylline 75% HPMC AS HF 15% TEC | 22.2 | 97.2 | 99.5 | | | | |
| 10% Theophylline 78.2% HPMC AS HF 11.8% ATBC | 14.8 | 92.1 | 98.8 | | | | |
| 10% Theophylline 69.2% Eudragit L100 20.8% TEC | 3.8 | 31.3 | 61.1 | | | | |

TABLE 8-continued

Drug release of melt extruded pellets (formulations according to invention are in bold type).

| Formulation | SGF 2 hrs | Buffer 45 min | Buffer 2 hrs | Buffer 4 hrs | Buffer 6 hrs | Buffer 8 hrs | Buffer 10 hrs |
|---|---|---|---|---|---|---|---|
| 10% Theophylline 69.2% Eudragit S100 20.8% TEC | 4.2 | 35.9 | 68.0 | 95.0 | | | |
| 10% Theophylline 64.3% Eudragit S100 25.7% TEC | 6.1 | 47.0 | 83.5 | 99.9 | | | |
| 20% Theophylline 57.1% Eudragit S100 22.9% TEC | 5.4 | 50.4 | 86.2 | 99.9 | | | |
| 30% Theophylline 50% Eudragit S100 20% TEC | 7.1 | 51.8 | 89.7 | 99.9 | | | |
| 40% Theophylline 42.9% Eudragit S100 17.1% TEC | 7.7 | 59.7 | 95.6 | 99.9 | | | |
| 30% Theophylline 50% Eudragit S100 20% ATBC | 5.8 | 32.9 | 63.7 | 84.5 | 91.9 | 97.0 | 98.8 |
| 30% Theophylline 50% Eudragit S100 20% PEG 8000 | 83.2 | 90.7 | 99.4 | | | | |
| 30% Theophylline 50% Eudragit S100 20% methylparaben | 3.9 | 61.6 | 97.8 | | | | |
| 30% Theophylline 70% Eudragit S100 | 5.9 | 31.3 | 56.1 | 81.6 | 92.3 | 97.8 | 98.8 |
| 30% Theophylline 60% Eudragit S100 10% TEC | 4.2 | 28.2 | 52.3 | 72.0 | 84.1 | 90.7 | 95.4 |
| 30% Theophylline 60% Eudragit S100 10% PEG 8000 | 18.2 | 41.3 | 72.4 | 90.5 | 97.3 | 98.5 | 99.2 |
| 30% Theophylline 60% Eudragit S100 10% methylparaben | 5.7 | 36.7 | 60.9 | 81.5 | 90.5 | 96.4 | 98.2 |

EXAMPLE 7

Hot-melt Extrusion of the Modified Release Multi-particulates

The following is an example for the hot-melt extrusion of a monolithic matrix with embedded enteric particles utilizing a Randcastle Microtruder RCP-0750. Various carrier polymers may be used, and the loading of multi-particulates may be varied.

TABLE 9

Composition for the hot-melt extrusion of a multi-particulate matrix.

| Component | Quantity [g] |
|---|---|
| Modified Release Multi-particulates | 30.0 |
| Carrier polymer | 70.0 |

Multi-particulates and the polymer were blended in a V-shell blender or alternative blending device. The formulation exhibits excellent flow properties and was fed through a hopper into the barrel by gravitational forces only without additional force feeding. The separation of the blend components inside the hopper or extruder was reduced due to the spherical nature of the particles and similarities in particle size and true density. The following processing conditions are used for the employed extruder. Variations in extrusion equipment, screw speed, temperature settings and motor load/torque are possible.

TABLE 10

Examples of carrier polymers and extrusion conditions using a Randcastle Microtruder RCP-0750.

| Polymer | Supplier & Grade | Melting Point [° C.] | Extrusion Temperature [° C.] | | | |
|---|---|---|---|---|---|---|
| | | | Zone 1 | Zone 2 | Zone 3 | Die |
| Poloxamer 188 | BASF, Lutrol F68 NF Prill | 57.1 ± 0.3 | 40 | 45 | 47 | 47 |
| Poloxamer 407 | BASF, Lutrol F127 NF Prill | 58.9 ± 0.2 | 40 | 45 | 50 | 48 |

TABLE 10-continued

Examples of carrier polymers and extrusion conditions using a Randcastle Microtruder RCP-0750.

| Polymer | Supplier & Grade | Melting Point [° C.] | Extrusion Temperature [° C.] | | | |
|---|---|---|---|---|---|---|
| | | | Zone 1 | Zone 2 | Zone 3 | Die |
| Polyethylene glycol 4000 | Dow, Carbowax Sentry PEG 4000 | 63.8 ± 0.3 | 40 | 45 | 50 | 50 |
| Polyethylene glycol 8000 | Dow, Carbowax Sentry PEG 8000 | 64.3 ± 0.5 | 40 | 50 | 55 | 55 |
| Polyoxyethylene 100K | Dow, Sentry Polyox WSR N10 | 69.7 ± 0.2 | 55 | 70 | 75 | 75 |
| Polyoxyethylene 200K | Dow, Sentry Polyox WSR N80 | 69.9 ± 0.8 | 55 | 70 | 75 | 75 |

EXAMPLE 8

Direct Compression of Multi-particulates

Functionally coated particles (30%), microcrystalline cellulose (Ceolus™ KG-802, 65%) and superdisintegrant (Ac-Di-Sol®, 5%) may be directly compressed into round tablets (333 mg, equivalent to 100 mg particles) using a single station manual Carver Press equipped with a concave, 10 mm diameter die. The compression force was 5 kN and the tablet hardness was 17.1±1.6 kP.

EXAMPLE 9

In vitro Method Drug Release Testing of Enteric Multi-particulates and Hot-Melt Extruded Matrices The drug release properties from the particles or hot-melt extruded matrices may be determined as described in USP 31, method <711> for delayed-release dosage forms method A. A paddle set-up (apparatus 2) was employed with a water bath to maintain the media temperature at 37±0.5° C. and the paddle speed set to 100 rpm. The formulations were placed in 750 ml simulated gastric fluid pH 1.2 (without pepsin, referred to as acid stage) for 2 hours and an aliquot of the fluid was withdrawn at the end of this period. A volume of 250 ml 0.20 M tribasic sodium phosphate that had been equilibrated to 37±0.5° C. was added after 2 hours to raise the pH of the media to 6.8 or 7.4, respectively (buffer stage). After expiration of the testing period, the remaining particles were completely destroyed by mixing with a high shear homogenizer to completely release residual drug, an aliquot of the fluid was filtered and analyzed to determine the total amount released using a validated HPLC method. All average values were obtained from at least n=3 and were reported as % released from the total amount released.

Figure 1:
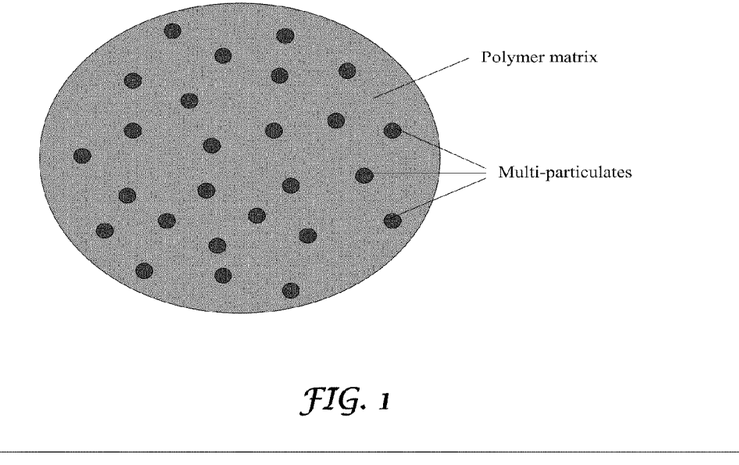
FIG. 1 shows a cross-section of an exemplary embodiment of a hot-melt extruded composition as provided by the invention.
Figure 2:
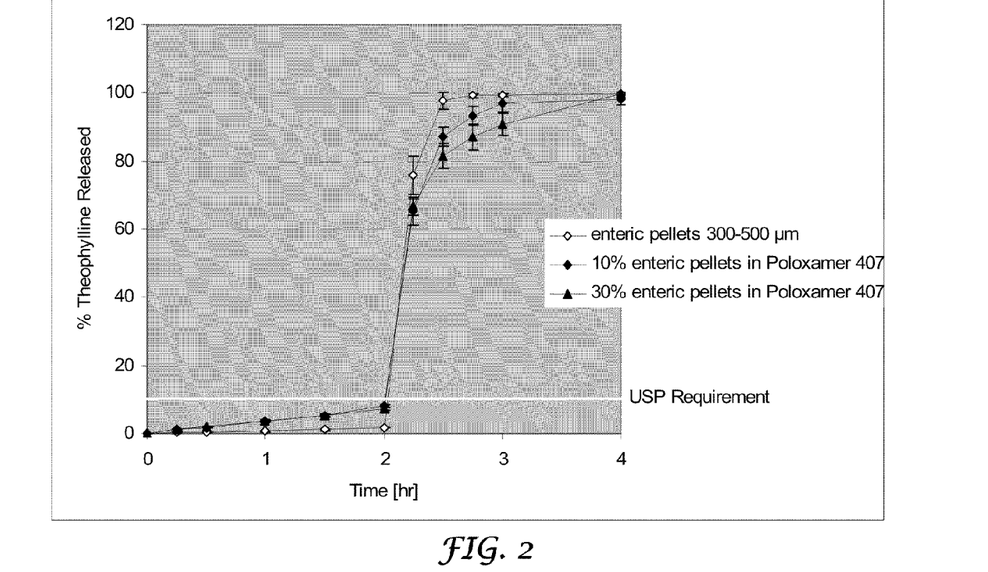
FIG. 2 is a graph of drug release profiles for compositions prepared according to Examples 2, 4 and 7 and tested according to Example 9.
Figure 3:
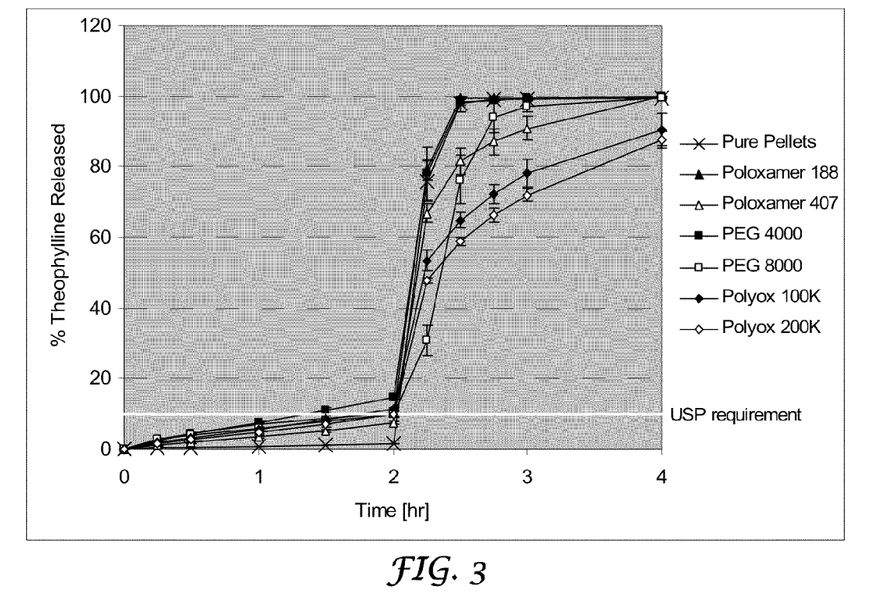
FIG. 3 is a graph of drug release profiles for compositions prepared according to Examples 2, 4 and 7 and tested according to Example 9. The pellet load in the matrix was 30%.
Figure 4:
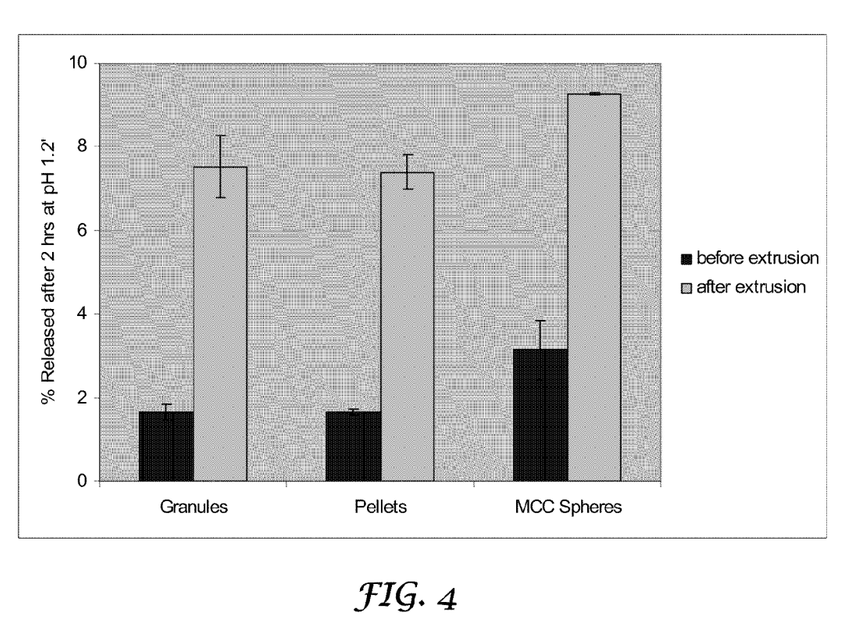
FIG. 4 shows the drug release after 2 hours in medium pH 1.2 for different multi-particulates according to Examples 1-4 and tested according to Example 9 before extrusion and after extrusion of 30% multi-particulates in Poloxamer 407 according to Example 7.
Figure 5:
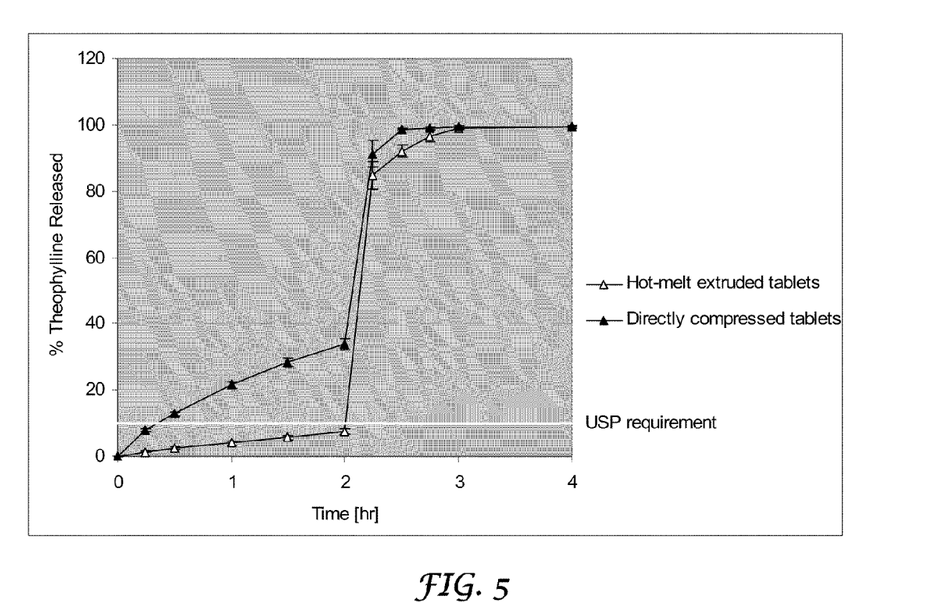
FIG. 5 is a graph of drug release profiles for compositions prepared with 30% granules as defined in Example 1 and coated according to Example 4 after processing according to Example 7 in Poloxamer 407 or Example 8 when tested according to Example 9.
Figure 6:
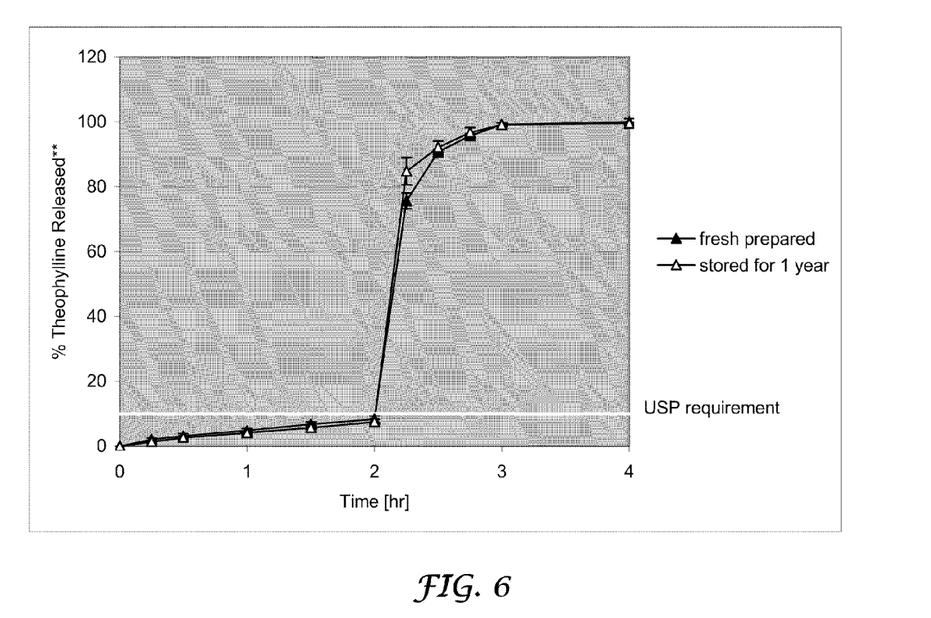
FIG. 6 is a graph of drug release profiles for a composition prepared with 30% granules as defined in Example 1 and coated according to Example 4 after processing according to Example 7 in Poloxamer 407 when tested according to Example 9 immediately after preparation and after 1 year of storage at room temperature (22±1° C.) and ambient relative humidity.

The dissolution behavior of the multi-particulates before and after extrusion into monolithic matrices is shown in FIGS. 2-5.

EXAMPLE 10

Determination of the Tensile Strength of Multi-particulates

The mechanical strength of the core material, coated multi-particulates and hot-melt extruded pellets was determined using a Chatillon Universal Tension/Compression tester model TCD-200. A flat circular steel plate was fitted onto a DFGS 50 digital force gauge and lowered in diametral direction towards the an individual particle at a crosshead speed of 2.5 mm/min. The load-deflection data was collected using Chatillon Nexygen TCD force testing software. The mechanical strength was reported as the tensile strength and calculated using the following equation:

$$\sigma = \frac{2P}{\pi dl}$$

Specimens with diameters (d) equaling the length (l) were selected for the experiments, and the maximum load (P) at which brittle fragmentation of the particles occurred was used for the calculations.

TABLE 11

Tensile strength of melt extruded Eudragit ® S100 pellets containing 30% theophylline as a function of plasticizer type and level. Diametral compression analysis of individual pellets (mean ± SD, n = 6).

| Plasticizer Concentration | Methylparaben Tensile Strength ± SD [MPa] | TEC Tensile Strength ± SD [MPa] | PEG 8000 Tensile Strength ± SD [MPa] |
|---|---|---|---|
| 0% | 40.4 ± 5.2 | 40.4 ± 5.2 | 40.4 ± 5.2 |
| 10% | 30.0 ± 3.0 | 27.0 ± 1.7 | 33.6 ± 2.1 |
| 20% | 29.5 ± 4.5 | 29.7 ± 2.4 | 17.4 ± 3.4 |

TABLE 12

Tensile strength of uncoated core material and coated multi-particulates. Diametral compression analysis of individual pellets (mean ± SD, n = 20).

| | Before Coating Tensile Strength ± SD [MPa] | After Coating Tensile Strength ± SD [MPa] |
|---|---|---|
| Granules | 7.3 ± 2.2 | 9.5 ± 2.8 |
| Pellets | 21.5 ± 3.0 | 20.0 ± 3.4 |
| MCC Spheres | 33.6 ± 5.4 | 24.1 ± 4.5 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 6,335,033: Melt-extrusion multiparticulates. Oshlack, B., Huang, H.-P., Chasin, M. (2002).

U.S. Pat. No. 6,743,442: Melt-extruded orally administrable opioid formulations. Oshlack, B., Chasin, M., Huang, H.-P., Sackler, D. (2004).

WO 2008/101743: Pellets comprising an active substance matrix resistant to gastric juice. Gryczke, A. (2008).

1. Young, C. R., Koleng, J. J., Ginity, J. W. M. Properties of drug-containing spherical pellets produced by a hot-melt extrusion and spheronization process. Journal of Microencapsulation 20: 613-625 (2003).

2. Young, C. R., Dietzsch, C., McGinity, J. W. Compression of Controlled-Release Pellets Produced by a Hot-Melt Extrusion and Spheronization Process. Pharmaceutical Development & Technology 10: 133-139 (2005b).

3. Follonier, N., Doelker, E., Cole, E. T. Evaluation of hot-melt extrusion as a new technique for the production of polymer-based pellets for sustained release capsules containing high loadings of freely soluble drugs. Drug Development and Industrial Pharmacy 20: 1323-1339 (1994).

4. de Brabander, C., Vervaet, C., Remon, J. P. Development and evaluation of sustained release mini-matrices prepared via hot melt extrusion. Journal of Controlled Release 89: 235-247 (2003).

5. Young, C. R., Crowley, M., Dietzsch, C., McGinity, J. W. Physicochemical properties of film-coated melt-extruded pellets. Journal of Microencapsulation 24: 57-71 (2007).

6. U.S. Pat. No. 0,055,52159: Solid depot drug form. Mueller, W., Spengler, R., Grabowski, S., Sanner, A. (1996).

7. Oshlack, B., Huan, H.-P., Chasin, M. (2001) US 2001/0033865, Melt-extrusion multiparticulates.

9. Lundqvist, Å. E. K., Podczeck, F. & Michael Newton, J. Compaction of, and drug release from, coated drug pellets mixed with other pellets. European Journal of Pharmaceutics and Biopharmaceutics 46, 369-379 (1998).

10. Beckert, T. E., Lehmann, K., Schmidt, P. C. Compression of enteric-coated pellets to disintegrating tablets. International Journal of Pharmaceutics 143, 13-23 (1996).

11. Dashevsky, A., Kolter, K., Bodmeier, R. Compression of pellets coated with various aqueous polymer dispersions. International Journal of Pharmaceutics 279, 19-26 (2004).

12. Altaf, S. A., Hoag, S. W., Ayres, J. W. Bead compacts. II. Evaluation of rapidly disintegrating nonsegregating compressed bead formulations. Drug Dev Ind Pharm 25, 635-642 (1999).

13. Vergote, G. J., Kiekens, F., Vervaet, C., Remon, J. P. Wax beads as cushioning agents during the compression of coated diltiazem pellets. European Journal of Pharmaceutical Sciences 17, 145-151 (2002).

14. Debunne, A., Vervaet, C. & Remon, J.-P. Development and in vitro evaluation of an enteric-coated multiparticulate drug delivery system for the administration of piroxicam to dogs. European Journal of Pharmaceutics and Biopharmaceutics 54, 343-348 (2002).

15. Debunne, A., Vervaet, C., Mangelings, D., Remon, J.-P. Compaction of enteric-coated pellets: influence of formulation and process parameters on tablet properties and in vivo evaluation. European Journal of Pharmaceutical Sciences 22, 305-314 (2004).

16. Tunón, Å., Alderborn, G. Granule deformation and densification during compression of binary mixtures of granules. International Journal of Pharmaceutics 222, 65-76 (2001).

17. Yao, T., Yamada, M., Yamahara, H., Yoshida, M. Tableting of Coated Particles. II. Influence of Particle Size of Pharmaceutical Additives on Protection of Coating Membrane from Mechanical Damage during Compression Process. Chemical & Pharmaceutical Bulletin 46, 826-830 (1998).

18. Altaf, S. A., Hoag, S. W., Ayres, J. W. Bead compacts. I. Effect of compression on maintenance of polymer coat integrity in multilayered bead formulations. Drug Dev Ind Pharm 24, 737-746 (1998).

19. El-Mahdi, I. M., Deasy, P. B. Tableting of coated ketoprofen pellets. Journal of Microencapsulation 17, 133-144 (2000).

20. Wagner, K. G., Krumme, M., Schmidt, P. C. Investigation of the pellet-distribution in single tablets via image analysis. European Journal of Pharmaceutics and Biopharmaceutics 47, 79-85 (1999).

21. Beckert, T. E., Lehmann, K., Schmidt, P. C. Compression of enteric-coated pellets to disintegrating tablets: uniformity of dosage units. Powder Technology 96, 248-254 (1998).

22. Schmidt, C., Bodmeier, R. A multiparticulate drug-delivery system based on pellets incorporated into congealable polyethylene glycol carrier materials. International Journal of Pharmaceutics 216: 9-16 (2001).

23. WO 2007/001451: Stabilized HME composition with small drug particles. Miller, D., McConville, J., McGinity, J. W., Williams, R. O. III (2007).

24. <711> Dissolution. in USP 31-NF (2008).

25. Young, C. R., Koleng, J. J., McGinity, J. W. Production of spherical pellets by a hot-melt extrusion and spheronization process. International Journal of Pharmaceutics 242: 87-92 (2002).

26. US 2007/0264328: Continuous melt spheronization apparatus and process for the production of pharmaceutical pellets. Ghebre-Sellassie, I., Martin, C., Elliot, B. (2007).

27. European Patent No. 1563897 Device for producing round pellets. Rein R. (2005).

What is claimed is:

1. A modified release pharmaceutical composition comprising an extruded thermoplastic polymer matrix in which modified release multi-particulate pellets are uniformly disposed, wherein the modified release multi-particulate pellets have a particle size of from 300 to 800 µm or an average particle size of from 300 to 3000 µm, and further wherein individual multi-particulate pellets comprise a modified release polymer matrix or a modified release polymer coating, and also further comprise an effective amount of one or more therapeutic compounds.

2. The composition of claim 1, wherein the extruded thermoplastic polymer matrix comprises at least 80% intact multi-particulate pellets by weight.

3. The composition of claim 1, wherein the extruded thermoplastic polymer matrix is hydrophilic.

4. The composition of claim 1, wherein a polymer of the extruded thermoplastic polymer matrix has a molecular weight of less than about 1,000,000 and is selected from the group consisting of poly(ethylene oxide), poly(ethylene glycol) or poly(ethylene oxide)-poly(propylene oxide) copolymer.

5. The composition of claim 1, wherein the multi-particulate pellets comprise 5 to 70 weight percent of the composition.

6. The composition of claim 1, wherein the multi-particulate pellets comprise an effective amount of 5 to 80 weight percent of one or more therapeutic compounds.

7. The composition of claim 1, wherein the modified release polymer is an enteric drug release polymer.

8. The composition of claim 1, wherein the multi-particulate pellets comprise between 10% to 60% (w/w) of the modified release polymer.

9. The composition of claim 1, wherein the multi-particulate pellets are film-coated drug granules, film-coated drug-loaded pellets or film-coated drug-layered nonpareils.

10. The composition of claim 1, wherein the multi-particulate pellets, or a component thereof, does not dissolve in the extruded thermoplastic polymer matrix.

11. The composition of claim 7, wherein less than 10% of the one or more therapeutic compounds will be released in acidic media from the composition, and wherein 80% of the one or more therapeutic compounds will be released in media pH above 6.8 according to USP 31, method 711 for delayed-release dosage forms method A.

12. The composition of claim 1, wherein the multi-particulate pellets have an average particle size of from 300 to 3000 µm.

13. The composition of claim 12, wherein the multi-particulate pellets have a particle size of from 300 to 800 µm and an average particle size of from about 300 to 3000 µm.

14. The composition of claim 1, wherein the multi-particulate pellets have a particle size of from 300 to 800 µm.

15. The composition of claim 1, further defined as a tablet.

16. The composition of claim 1, wherein the modified release polymer is further defined as immediate, extended, sustained or delayed release polymer.

* * * * *